(12) United States Patent
Mannheimer

(10) Patent No.: US 6,754,516 B2
(45) Date of Patent: Jun. 22, 2004

(54) NUISANCE ALARM REDUCTIONS IN A PHYSIOLOGICAL MONITOR

(75) Inventor: Paul D. Mannheimer, Danville, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 0 days.

(21) Appl. No.: 09/910,700

(22) Filed: Jul. 19, 2001

(65) Prior Publication Data

US 2003/0018241 A1 Jan. 23, 2003

(51) Int. Cl.[7] .................................................. A61B 5/00
(52) U.S. Cl. ....................... 600/323; 600/309; 600/502; 600/504
(58) Field of Search ................................ 600/309–310, 600/322–326, 500–504; 356/39–42

(56) References Cited

U.S. PATENT DOCUMENTS

| 4,094,320 A |   | 6/1978  | Newton et al. |         |
|-------------|---|---------|---------------|---------|
| 4,403,215 A | * | 9/1983  | Hofmann et al. | 340/573 |
| 4,653,498 A |   | 3/1987  | New, Jr. et al. |        |
| 4,911,167 A |   | 3/1990  | Corenman et al. |       |
| 5,243,998 A | * | 9/1993  | Silverman et al. | 600/595 |
| 5,348,004 A |   | 9/1994  | Hollub         |        |
| 5,464,012 A | * | 11/1995 | Falcone        | 600/301 |
| 5,469,144 A |   | 11/1995 | Gradzki et al. |        |
| 5,638,818 A | * | 6/1997  | Diab et al.    | 600/476 |
| 5,645,059 A |   | 7/1997  | Fein et al.    |        |
| 5,853,364 A |   | 12/1998 | Baker, Jr. et al. |     |
| 5,865,736 A | * | 2/1999  | Baker, Jr. et al. | 600/323 |
| 5,954,668 A | * | 9/1999  | Uber, III et al. | 600/549 |
| 6,047,201 A | * | 4/2000  | Jackson, III   | 600/344 |
| 6,241,661 B1 | * | 6/2001 | Schluess et al. | 600/300 |
| 6,266,565 B1 | * | 7/2001 | Er et al.      | 607/27 |
| 6,354,991 B1 | * | 3/2002 | Gross et al.   | 600/29 |
| 6,397,100 B2 | * | 5/2002 | Stadler et al. | 600/509 |

FOREIGN PATENT DOCUMENTS

EP 0 909 551 A1 4/1999

OTHER PUBLICATIONS

Bai, et al., *IEEE Transactions on Information Technology ini Biomedicine*, 3(3):197–204 (1999).

Trang, et al., "Masimo SetR Pulse Oximetry Improves Detection of Sleep Apnea–Related Hypoxemia," Abstract, May 21, 2001.

* cited by examiner

Primary Examiner—Max F. Hindenburg
Assistant Examiner—Matthew Kremer
(74) Attorney, Agent, or Firm—Townsend & Townsend & Crew LLP

(57) ABSTRACT

A method and apparatus for controlling alarms in a medical diagnostic apparatus where an alarm is generated when a measured value for a physiological parameter is outside a specified range. The method continuously calculates a baseline value, and establishes dynamic thresholds that are related to and continuously track the baseline value. The method determines the amount of time the measured value is past the dynamic threshold, and the amount by which the threshold is passed. Alarms are triggered based upon a combination of the amount of time and the amount by which the threshold is passed. Preferably, the combination is an integral or some function of an integral.

17 Claims, 4 Drawing Sheets

NUISANCE ALARM REDUCTIONS IN A PHYSIOLOGICAL MONITOR

BACKGROUND OF THE INVENTION

The present invention relates to alarms in medical diagnostics apparatus, and in particular to improvements in reducing nuisance alarms for pulse oximeters.

A typical pulse oximeter measures two physiological parameters, percent oxygen saturation of arterial blood hemoglobin ($SpO_2$) and pulse rate. For alarm purposes, low and high thresholds are set for both $SpO_2$ and pulse rate, defining normal ranges within which it is desired to maintain the patient. For example, with a neonate it might be desired that sat should remain between 85 and 95 percent and pulse rate should remain between 120 and 170 beats per minute. From the two measured parameters, typically four alarm types can be generated, low sat, high sat, low rate, and high rate. In some pulse oximeters, an alarm begins immediately when either sat or rate goes outside the normal range and the alarm ends immediately when both sat and rate return within the normal range. Alarms are typically announced by audible and/or visual indicators. Alarms, which are dependent on the instantaneous excursions of a measured value outside a range, are commonly referred to as conventional alarms.

Each occurrence in which a measured parameter goes outside the normal range is referred to as an event. Thus, in a typical pulse oximeter, each event coincides with an alarm, and the alarm duration may be identical to the event duration. Some of the alarms produced by typical pulse oximeters are not generally considered to correspond to events that are clinically significant. The exact definition of clinical significance varies depending on the patient and circumstances, but is in general related to the severity and duration of the event of interest. For example, a very shallow desaturation might only be considered significant if sustained for a relatively long period of time. Likewise, a desaturation of very brief duration might only be considered significant if it falls very deep below the low sat threshold. In addition to clinically insignificant alarms, parameter measurement error due to noise, signal artifact or bias can also produce false events and trigger alarms. An alarm that does not correspond to a clinically significant event may be considered a nuisance alarm.

Several approaches are available which attempt to reduce the number of nuisance alarms. Some of these approaches have either looked at lowering the alarm threshold or waiting some fixed period of time after the threshold has been crossed before triggering an alarm. Lowering the threshold can be problematic because a patient's blood oxygen saturation can remain indefinitely below the original threshold, but above the new threshold, and an alarm will never be generated. Delaying alarm generation by a fixed amount of time is also problematic due to a potentially serious situation in which a patient's saturation abruptly falls to and remains at a very low level, requiring prompt medical attention.

Another solution to the nuisance alarm problem is described in U.S. Pat. No. 5,865,736, entitled, "METHOD AND APPARATUS FOR NUISANCE ALARM REDUCTIONS," assigned to the assignee herein. The solution described by the '736 patent is commercially known as the SatSeconds™ Alarm Management Technology ("SatSecond") feature. The SatSecond concept has been incorporated into some of assignee's pulse oximeters, such as the model N-395 pulse oximeter, for enhanced alarm management. FIG. 1 is a graph illustrating the alarm response according to this known SatSecond approach. This figure shows a conventional and the SatSeconds alarm management methods. This figure, for illustration purposes shows the methods applied to $SpO_2$ measurements. As described above and shown in FIG. 1, with conventional alarms, $SpO^2$ (4) or pulse rate (not shown) readings that fall below a specified fixed lower threshold 6 or above a specified fixed upper threshold (not shown) trigger an audible or visible alarm state. With the SatSecond methodology, an alarm state is entered only when the second-by-second accumulated product 2, of time and the degree to which the $SpO_2$ (4) exceeds the lower 6 or upper (not shown) specified threshold, equals or exceeds an integrated threshold 8. Both the conventional and SatSecond alarm management methods are equally applicable to pulse rate or other physiological measurements.

The motivation for the SatSecond method is to reduce the number of nuisance alarms in which a measured value such as $SpO_2$ is beyond an alarm threshold, but does not represent a clinically significant event. For example, if a caregiver feels that a desaturation of less than 5 points below the lower alarm threshold for less than 5 seconds is not clinically meaningful, but rather constitutes a nuisance, the caregiver may set the SatSecond alarm threshold to "25" (5 points for 5 seconds). Then only a deeper desaturation of longer duration (i.e., a product that exceeds 25 SatSeconds) will initiate an alarm. In certain pulse oximeter models manufactured by the assignee herein, the product of saturation-below-the-threshold and time are accumulated once per second, and this product is compared to the SatSecond alarm threshold each time is it calculated. The effect of using the SatSecond alarm management method is to reduce the number of nuisance alarms and to alarm more specifically in response to events that are clinically meaningful as established previously by the caregiver.

A limitation in the use of the each of these prior art methods occurs when the $SpO_2$ value (or other measured value) is systematically in error, as in where there is a high or low bias in the measured value, even if the bias error is relatively small. Using the SatSecond method as an example, this limitation is illustrated in FIG. 2. The graph 22 shows a monitored value of $SpO_2$ having a bias of a few points high relative to the true saturation 21. As the desaturation event 25 occurs, the lower alarm threshold 24 is not reached until later in the event, if at all, and the $SpO_2$ value dips only slightly below the threshold 24. Accordingly, the SatSecond value 28 (which corresponds to the area of the dark hatched region 26 of the upper curve 22 below the lower alarm threshold 24) never achieves the necessary level 29 needed to initiate an alarm state. FIG. 2 provides an illustration of a "missed" SatSecond alarm due to a bias in the $SpO_2$ readings. The erroneously high $SpO_2$ value may interfere with the ability to accurately calculate the proper value of the SatSecond integral 28. The converse (i.e., false SatSecond alarm) would occur if the $SpO_2$ readings were too low due to a low bias. Hence, $SpO_2$ bias affects the reliability of measured values and alarms based on those values.

Ideally, the $SpO_2$ reading will be proper (i.e., unbiased from the true $SaO_2$). However, under some circumstances such a bias can and does occur. It is known that bias can be created, for example, by an improperly placed sensor that shunts light between the emitter and the detector, or by a sensor that has been applied too tightly, or a by patient with significant edema. Additionally, sensor placement variations, as well as other factors introduce bias, such that even instrument specifications acknowledge the presence of bias. Specifically, the accuracy specification for pulse oximetry sensors readily allows a bias between two sensors placed on the same patient of 3 sat-points. Under such circumstances (i.e., two sensors placed on the same patient), one sensor may indicate an alarm state, while the other does not, resulting in ambiguity in not knowing which sensor is providing the more correct reading. Thus, although the SatSecond invention greatly reduces nuisance alarms in pulse oximeter readings, the measurements and hence alarm events may still be susceptible to bias-induced nuisance alarms. Moreover, the SatSecond improvement is based on a product of saturation-below-a-fixed threshold (or above) and time. This fixed threshold can also be problematic, as is described below.

Alarm thresholds described thus far are based on fixed windows, where a window is defined by the region between a fixed lower and a fixed upper alarm threshold. The fixed lower and upper threshold values are based on typical default values used for patients in general, and which may be set by the caregiver irrespective of the current instrument readings. However, the fixed window approach may be problematic for patients having, for example, a chronically elevated pulse rate value. Some prior art pulse oximeters manufactured by the assignee herein offered a feature known as "Smart Alarms" to allow caregivers to quickly establish the lower and upper conventional alarm thresholds by manually pressing a button on the oximeter unit. The "Smart Alarm" is essentially a fixed relative threshold based on a current physiological value that is being monitored. Using this "Smart Alarm" feature, the conventional alarm thresholds could be established at a preset value above and below the current readings of pulse rate, as opposed to the fixed default values typically used for patients in general. Thus if a patient is chronically at an elevated pulse rate, a revised fixed threshold relative to the current readings could be easily set to a preset number below the current reading so as not to alarm unnecessarily. While the "Smart Alarm" approach allows for the setting of a new fixed threshold that is related to the then current readings, it is still a fixed threshold and hence suffers from the same shortcomings described thus far.

There is therefore a need for improvements in medical diagnostic devices, and in particular to improvements in both integrated or "product"-type and relative-deviation threshold alarms for pulse oximeters.

SUMMARY OF THE INVENTION

The present invention provide a method and apparatus for controlling alarms in a medical diagnostic apparatus where an alarm is generated when a measured value for a physiological parameter is outside a specified range. The method continuously calculates a baseline value, and establishes dynamic thresholds that are related to and continuously track the baseline value, and triggers an alarm when a measured value exceeds the dynamic and continuously tracking threshold. In a preferred embodiment, the method determines the amount of time the measured value is beyond the dynamic threshold, and the amount by which the threshold is passed, and triggers an alarms based upon a combination of the amount of time and the amount by which the threshold is passed. Preferably, the combination is an integral or some function of an integral.

In one aspect directed to saturation alarms on a pulse oximeter, an alarm is generated when the measured saturation value falls above or below a baseline-tracking dynamically changing upper or lower threshold respectively.

In another aspect, the preferred embodiment of this invention calculates the integral of the amount by which a measured value of the oxygen saturation exceeds an upper baseline-tracking dynamically determined threshold, or falls below a lower baseline-tracking dynamically determined threshold. A saturation alarm is generated when the integral exceeds a predetermined value. Similarly, for a pulse rate alarm on a pulse oximeter, the preferred embodiment of this invention calculates the integral of the amount by which a measured value of the pulse rate exceeds an upper baseline-tracking dynamically-determined threshold, or falls below a lower baseline-tracking dynamically-determined threshold, and a pulse rate alarm is generated when the integral exceeds a predetermined value. The relative-threshold-based alarm management method of the present invention may also be combined with a fixed threshold alarm scheme.

For a further understanding of the nature and advantages of the invention, reference should be made to the following description taken in conjunction with the accompanying drawings.

DESCRIPTION OF THE SPECIFIC EMBODIMENTS

Embodiments of the present invention relate to increasing the reliability of alarms in medical diagnostic equipment measuring a physiological parameter by improving reductions in nuisance alarms. In order to illustrate the invention, the example of a pulse oximeter with thresholds for blood oxygen saturation ($SpO_2$) will be described. In particular, a low saturation event is described. Alternately, high saturation, low pulse rate, high pulse rate or other alarm parameters could be addressed by the present invention. In addition, the invention could be used for other types of medical diagnostic equipment.

Figure 3:
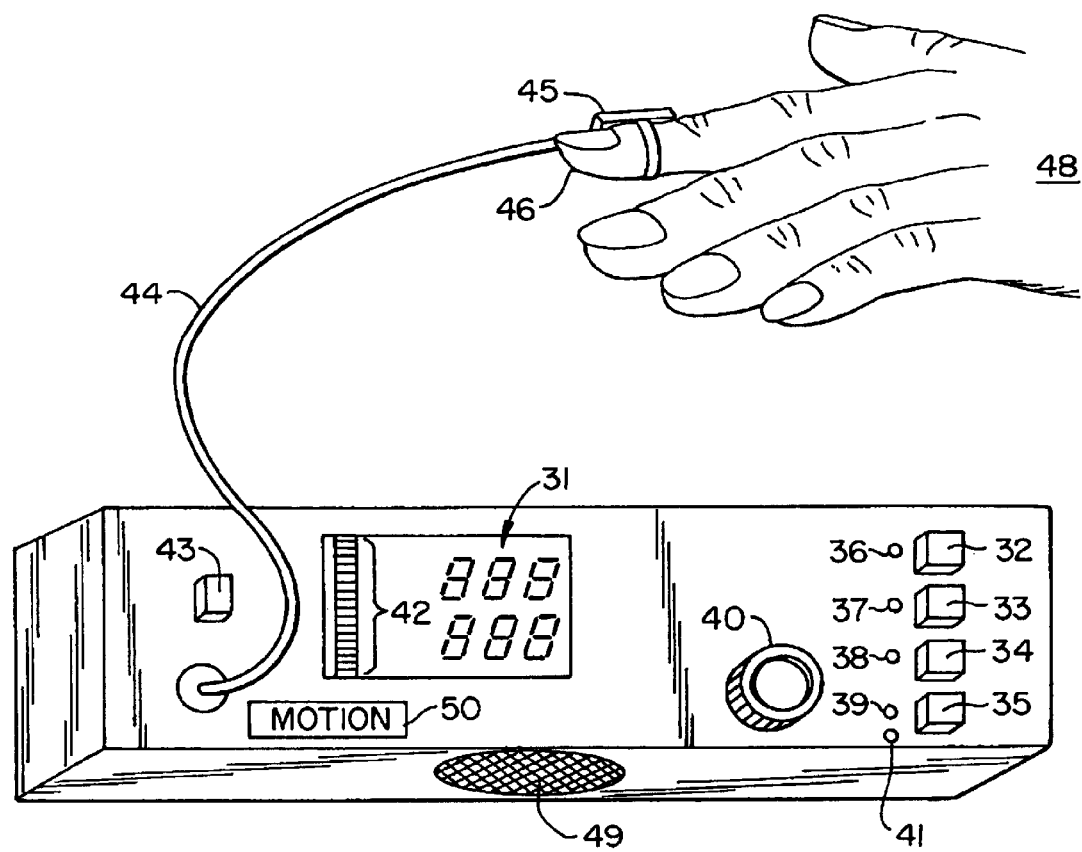
FIG. 3 is a diagram of an example pulse oximeter.

FIG. 3 illustrates a typical pulse oximeter. FIG. 3 illustrates the oximeter housing which includes a digital display 31, select buttons 32–35, alarm status lights 36–39, and adjustment knob 40, synchronization status light 41, LED digital view meter 42, and power switch 43. A cable 44 to the sensor 45 is shown with the sensor attached to a finger 46 on a patient's hand 48.

An alarm in accordance with the embodiment of the present invention can be either produced audibly through a speaker 49, or produced on one of the displays described above. Also shown is a display 50 for providing an indication of motion distorting the signal, which could also generate an alarm condition. The display 50 and/or display 31 are also used to provide other information to the clinician as is deemed necessary. The pulse oximeter shown in FIG. 3 is shown for exemplary purposes and is not meant to limit the embodiments of the present invention. For example, the sensor 45 can be replaced by other appropriate sensors for use at other tissue locations including but not limited to the ear, foot, forehead and nose of adult, infant, neonatal and perinatal patients.

Figure 1:
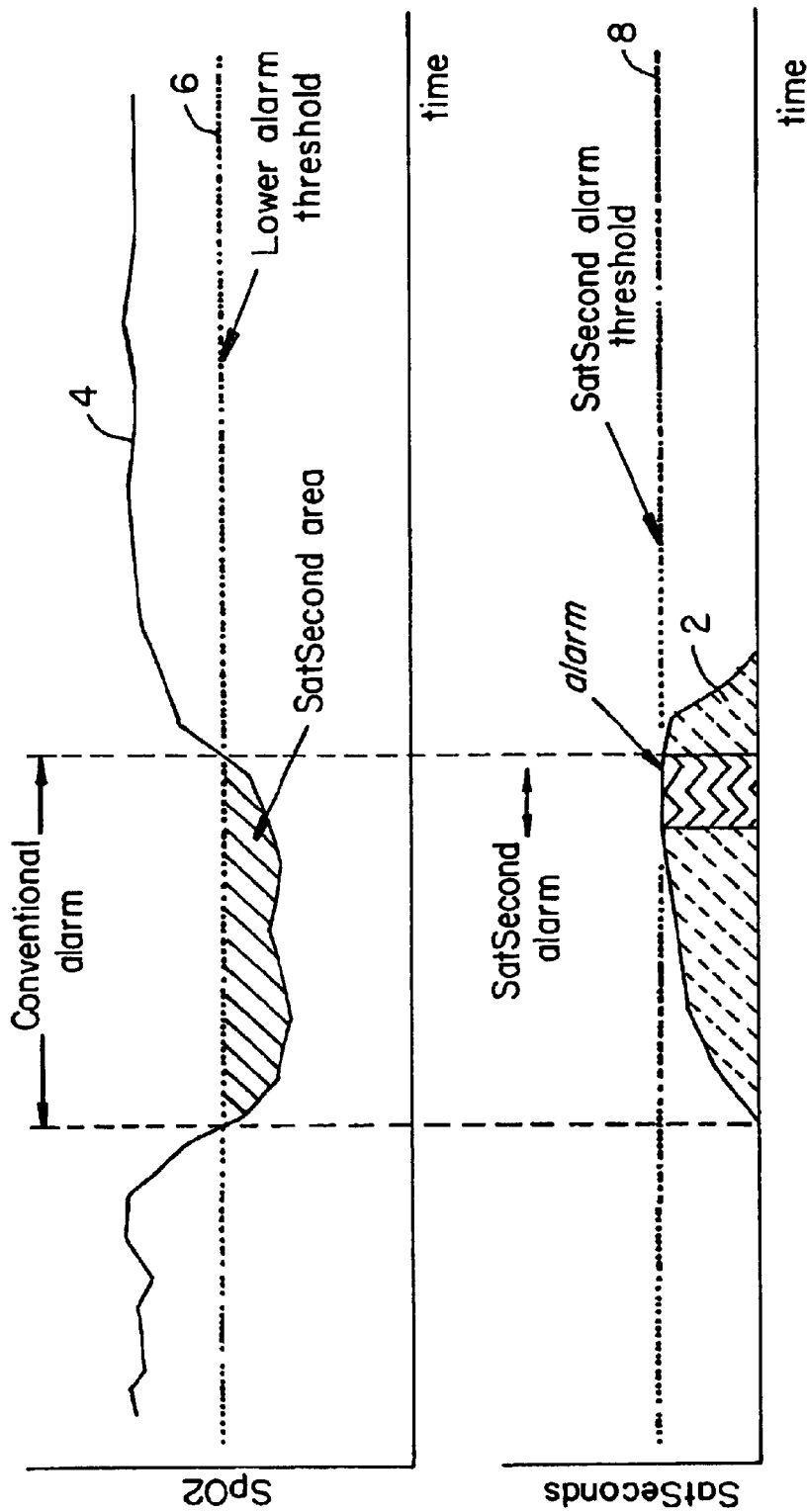
FIG. 1 a graph illustrating prior art conventional and SatSeconds™ Alarm Management Technology alarm management methods.
Figure 2:
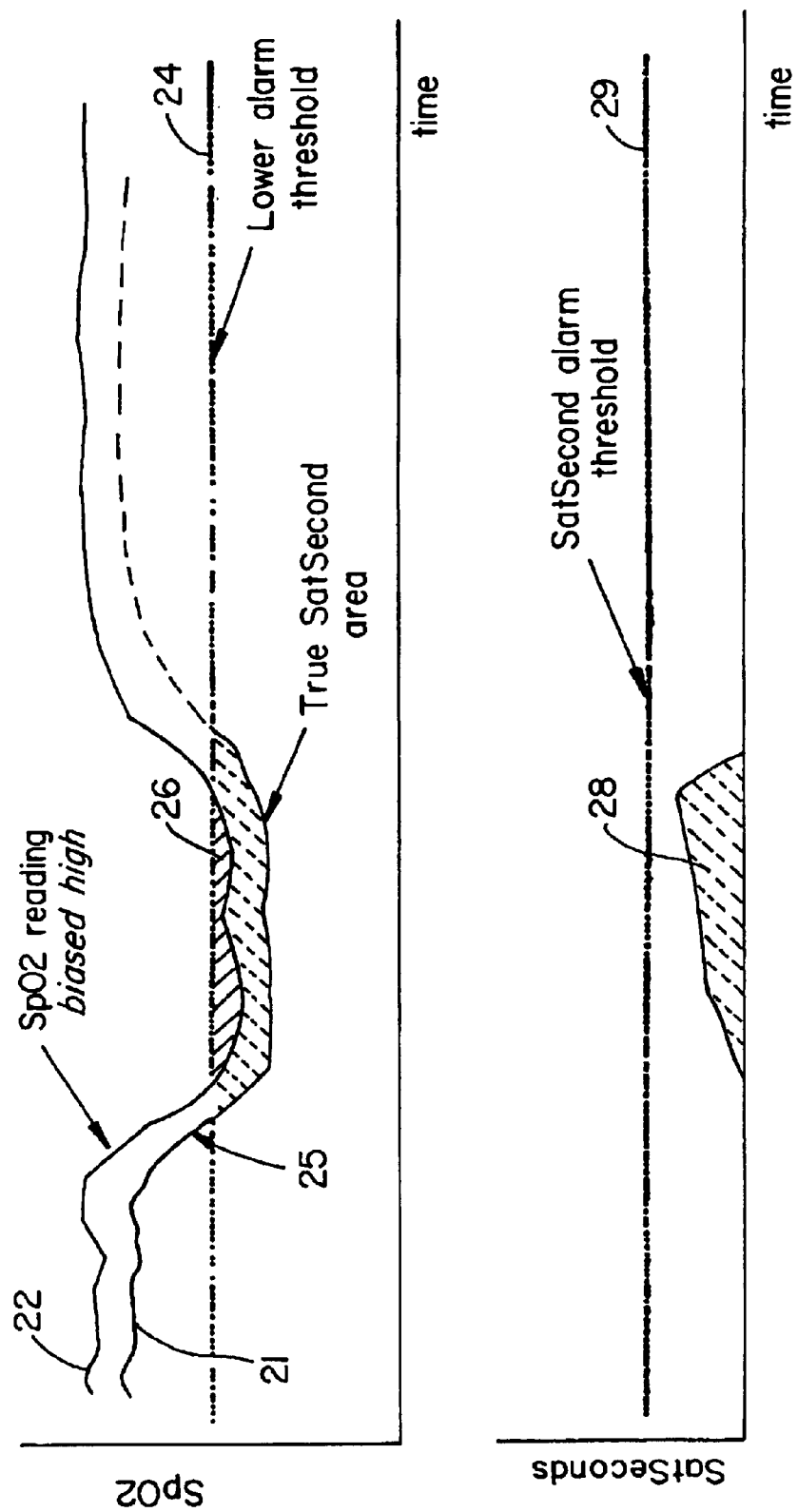
FIG. 2 is a graph illustrating a missed SatSecond™ alarm due to $SpO_2$ bias.

An example of an electronic circuitry for a pulse oximeter which may be configured to incorporate the embodiment of the present invention is provided as FIG. 2 of U.S. Pat. No. 5,865,736, entitled: "METHOD AND APPARATUS FOR NUISANCE ALARM REDUCTIONS," assigned to the assignee herein, the disclosure of which is hereby incorporated herein in its entirety. U.S. Pat. No. 5,865,736 also describes algorithms used to calculate the integral of the difference between the current saturation and a saturation threshold whenever the current saturation is below the saturation threshold, as well as any necessary additional logic related to resetting and clearing the integral and the alarm.

Oxygen saturation can be estimated using various techniques. In one common technique, the photocurrent generated by the photo-detector is conditioned and processed to determine the modulation ratio of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990. The relationship between oxygen saturation and modulation ratio is further described in U.S. Pat. No. 5,645,059, entitled "MEDICAL SENSOR WITH MODULATED ENCODING SCHEME," issued Jul. 8, 1997. An electronic processor for calculating in vivo blood oxygenation levels using pulsed light is described in U.S. Pat. No. 5,348,004, entitled "ELECTRONIC PROCESSOR FOR PULSE OXIMETER," issued Sep. 20, 1994, and a display monitor for a pulse oximeter is described in U.S. Pat. No. 4,653,498, entitled "PULSE OXIMETER MONITOR," issued Mar. 31, 1987. All five patents are assigned to the assignee of the present invention and incorporated herein by reference.

The brief description of pulse oximeters, and associated electronic circuitry and algorithms described above serve as a contextual fabric for describing the alarm management method according to embodiments of the present invention, which are described below.

Figure 4:
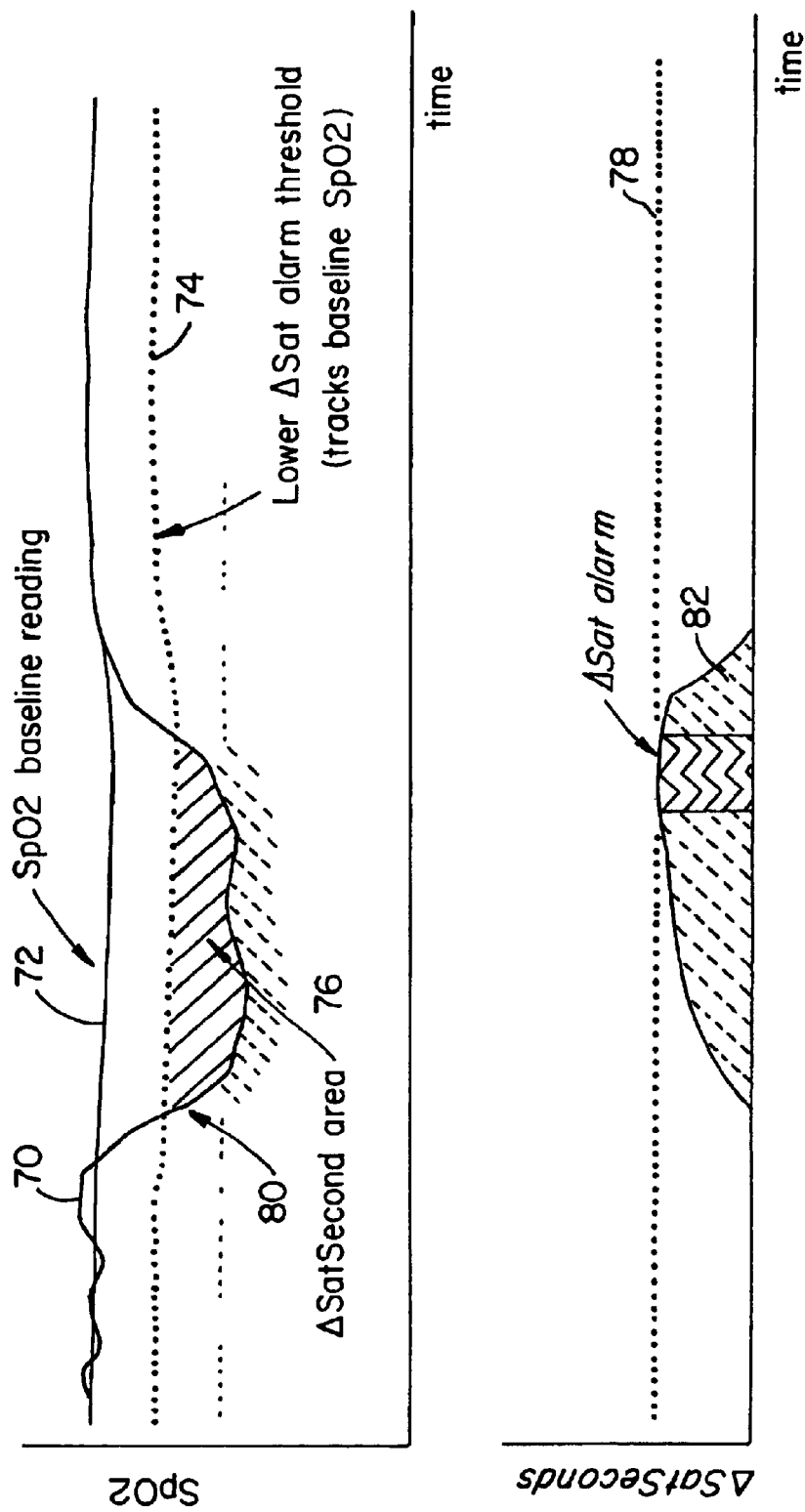
FIG. 4 is a graph illustrating the alarm management method according to embodiments of the present invention.

FIG. 4 illustrates the behavior of the alarm management method according to embodiments of this invention. In one embodiment of the present invention, an alarm is generated when saturation signal 70 falls below the baseline tracking saturation threshold 74.

In an alternate embodiment, the alarm management method is based on an integrated-relative-threshold algorithm. A saturation signal 70 is compared to a low sat threshold 74. Also illustrated is an integral threshold 78. An excursion 80 produces an integral value 82 that can exceed the integral threshold 78. The value 82 is a product of the amount of time and the amount by which the measured value of oxygen saturation exceeds the threshold. The alarm management method according to embodiments of this invention include dynamically and continuously calculating a "baseline" value 72 for the $SpO_2$ readings, and establishing a continuously and dynamically tracking set of upper (not shown) and lower alarm threshold 74 that continuously and dynamically follow this baseline. Certain embodiments first calculate a baseline value for saturation or other physiological parameter of interest, and define the dynamic thresholds by offsetting from this baseline. As the instantaneous readings of $SpO^2$ (or other variable) wander beyond these thresholds, the product 82 of time and extent beyond the threshold is calculated. The low sat alarm threshold 74 tracks the baseline $SpO_2$ trend 72. The baseline trend 72 is an average of the measured $SpO_2$ signal 70, and which is obtained by low-pass filtering the measured $SpO_2$ signal 70. The area under the curve 76 where the instantaneous $SpO_2$ value drops below the lower threshold 74 is calculated ($\Delta$SatSeconds) and an alarm state is entered when the value 82 of the integral equals or exceeds a user defined integral threshold 78. Alternately, a default value may be used in lieu of the user-defined threshold 78.

In one embodiment, the baseline value 72, which the upper (not shown) and lower thresholds 74 track, is computed by using a low-pass filter. Alternately, the baseline is calculated using a running median filter. Other alternate methods for calculating a baseline may also be used so long as the methodology results in a more slowly varying value for the baseline than the instantaneous readings 70. Examples of these alternate methods are described below.

In one alternate embodiment, an "Infinite Impulse Response" filter is used by continuously updating the baseline value using the most recent reading added to the running computation of the past, as shown in Eqn. 1 below:

$$\text{Baseline Value} = 1/N * SpO_2 + (N-1)/N * \text{Last Baseline Value}, \quad \text{Eqn. 1}$$

where N is a number that results in a "slow" response time (e.g. 15 minutes)

In another alternate embodiment, the baseline is tracked by using a running "Finite Impulse Response" filter, where readings taken over a past several minutes are stored and averaged. These baseline-tracking methods are examples of tracking algorithms, and are not meant to limit the embodiments of the present invention, as many methods are available for calculating the baseline $SpO_2$ value.

In the embodiments of the present invention, alarm thresholds are dynamic and determined relative to the tracked baseline. In the prior art integral-based methods referred to and described as the SatSecond concept, the (integral value) alarm threshold is calculated based on instantaneous readings wandering beyond fixed thresholds established by default values or user-specified upper and lower alarm thresholds. In the methods embodied by the present invention, the threshold dynamically follows a dynamically calculated baseline, trending up or down with the measured value, while the baseline dynamically smoothes out the short-lived excursions in the $SpO_2$ signal. In other words, a window is established by defining upper and lower threshold values that are offset from the baseline by a specified value above and below the baseline respectively, thus establishing a relative threshold. In this way, any bias that exists between measured $SpO_2$ and true $SaO_2$ has minimal effect on the reliability of saturation alarms.

In other embodiments, the dynamic alarm threshold is an offset of a continuously updated baseline, so that the alarm threshold is directly computed in one step, as opposed to calculating a baseline in a first step and then offsetting the baseline to determine the threshold in a second step. This is achieved by offsetting a slowly varying average of the measured value by a certain amount above and below the measured value to define upper and lower relative thresholds respectively.

The improved alarm management methodology, as embodied by the present invention can be used independently, or in conjunction with a fixed window method, with the combined alarm thresholds chosen to complement one another. The following examples, described below demonstrate the utility of the improvements as embodied by the present invention.

EXAMPLES OF $SpO_2$ MONITORING SCENARIOS

The following assumptions apply to each of the following examples:

The baseline true value of $SaO_2$ is 95%,

The fixed alarm threshold is set to 85% and the SatSecond (SS) value needed to trigger an alarm is set to 25 sat-second, the $\Delta$SatSecond ($\Delta$SS), relative-threshold is set to 25 based on a threshold of 10% less than a running baseline, integrated products of deviation-from-threshold times time are calculated once every second.

Thus the thresholds are nominally equal (i.e., a drop in sat of 10%), but the $\Delta$SS alarm triggers based on the change from a baseline, while the SS alarm triggers based on crossing the fixed value of 85% $SpO_2$ (i.e., 10% drop from the 95% true baseline value).

Example 1

Correct $SpO_2$ Readings

This example involves a scenario where the $SpO_2$ readings are correct, or in other words, the $SpO_2$ and $SaO_2$ readings are equivalent, since no measurement bias is present. In this example, if the $SaO_2$ value drops 2 points below the fixed threshold (83% $SaO_2$ and $SpO_2$), the SS alarm will sounds in 13 seconds (13 sec*2 sat deviation=26 sat-seconds, which is greater than 25 sat seconds). The $\Delta$SS level triggers at an equivalent point, but is redundant. Both trigger events represent True Positives (TP). A Positive event is an event where the diagnostic device triggers an alarm. A "True" condition refers to the real and actual data supporting the presence of an alarm condition. Thus a TP event is where the diagnostic device senses an event and triggers an alarm where a real clinically significant event was present. A TP event represents an event where the diagnostic device has correctly identified a clinically significant event and triggered an alarm.

If the $SaO_2$ drops to 2 points above the fixed threshold (87%), neither alarm will sound as $SpO_2$ does not cross either of the thresholds. Both non-trigger events will then represent True Negatives (TN). A Negative event is an event where the diagnostic device does not trigger an alarm. Thus a TN event is where the diagnostic device does not and should not trigger an alarm. A TN event represents an event where the diagnostic device has correctly identified a non-existent or clinically insignificant event and does not trigger an alarm.

Example 2

Positively Biased $SpO_2$ Readings

This example involves a scenario where the $SpO_2$ baseline reads 98%, 3 points high relative to the true $SaO_2$ value due to a reading with positive bias. In this example, if the $SaO_2$ value drops 12 points, that is 2 points below the threshold (83%), an alarm state should occur in 13 seconds (13 sec*2 sat deviation=26 sat-seconds, which is greater than 25 sat seconds), but does not due to the bias resulting in a $SpO_2$ reading of 86%. This results in a False Negative (FN) for the SatSecond (SS) threshold. A "False" event refers to a state sensed by the diagnostic device that is not supported by the real and actual data. Thus a FN event is where a diagnostic device should trigger an alarm but does not. A FN event represents an event where the diagnostic device has missed a clinically significant event and not triggered an alarm. In this example, the SS alarm would never occur since the $SpO_2$ value never drops below 85%. Further, a conventional $SpO_2$ set to less than 85% would also miss this event.

Since $SpO_2$ drops by 12 points, this will result in an $\Delta$SS alarm in 13 seconds (2 points below the dynamic alarm threshold for 13 seconds=26 $\Delta$SS). This event will then be a True Positive for $\Delta$SS. This example clearly points out the improvement provided by the relative sat-second method over the fixed sat-second method for a case where the measurements are positively biased, since the fixed threshold alarm would miss the event, but a relative and dynamic alarm threshold would capture the event.

If $SaO_2$ drops 8 points, to two points above the threshold (87%), $SpO_2$ readings become 90% (98%–8%) and no SS alarm would sound, thus resulting in a True Negative event. The same result occurs with $\Delta$SS, as the 8-point drop isn't sufficient to trigger the $\Delta$SS integral. Recall that the $\Delta$SS relative-threshold is set to 25 based on a threshold of 10% less than a running baseline.

Example 3

Negatively Biased $SpO_2$ Readings

This example involves a scenario where the $SpO_2$ baseline reads 92%, 3 points low relative to the true $SaO_2$ value due to a negatively biased reading. In this example, if the $SaO_2$ drops 12 points, 2 points below the fixed threshold (83%), with the $SpO_2$ reading 80% due to the negative bias, the SS alarm is triggered after 5 seconds (5 points below threshold*5 seconds=25 SS). The ASS alarm will trigger in 13 seconds (2 points below the 10 point allowable threshold takes 13 seconds to exceed 25 $\Delta$sat-seconds). Thus this scenario results in a TP for both alarm methods, though a little sooner than required for the fixed SS alarm.

If the $SaO_2$ drops 8 points, 2 points above the fixed threshold (87%), the SS alarm should never engage, but it does trigger a FP in 25 seconds due to the 3-point low bias ($SpO_2$=84%). The $SpO_2$ drop from 92% to 84% does not trigger an $\Delta$SS alarm since it does not exceed the 10% necessary threshold drop. Here the advantage of the improved alarm management is illustrated since this clinically insignificant event (by definition) would trigger a FP SS alarm, and hence create an unnecessary or a nuisance alarm, while the dynamic threshold design ($\Delta$SS) registers a TN.

As can be seen from these examples, the sensitivity and specificity for the dynamic and continuous baseline tracking approach is improved in the presence of bias over a fixed threshold approach. Particularly, the relative-dynamic threshold method as embodied in this invention is especially adept at capturing clinically significant events in cases where the diagnostic device's readings are positively biased. When no bias is present, both the dynamic and fixed threshold approaches are equivalent in their sensitivity.

Alternate embodiments of this invention combine both the dynamic relative threshold methods as embodied by this invention and the known fixed threshold methods. This combined embodiment is especially useful where the diagnostic device is configured to prevent a slowly decaying baseline $SaO_2$ (and thus $SpO_2$) from falsely missing hypoxia. In such an embodiment, the fixed threshold is set at a lower value so as to avoid false positives, however, the lower fixed threshold is judiciously set to catch a potentially slowly deteriorating patient condition. This arrangement is useful because a dynamic and relative baseline tracking alarm management scheme would also slowly track the decaying baseline and thus not trigger a low saturation alarm.

As will be understood by those of skill in the art, the present invention which is related to calculating an integral of the time and depth product of a monitored variable, using a dynamically tracking threshold for initiating and calculating an integral, may be embodied in other specific forms without departing from the essential characteristics thereof. For example, variables other than $SpO_2$ such as pulse rate, blood pressure, temperature, or any other physiological variable could be continuously or periodically tracked. Accordingly, the foregoing disclosure is intended to be illustrative, but not limiting, of the scope of the invention, which is set forth in the following claims.

What is claimed is:

1. A method for controlling an alarm in a medical diagnostic apparatus, said apparatus monitoring a measured value, said method comprising:
   measuring a value of a physiological parameter;
   automatically establishing a dynamic threshold value, wherein said dynamic threshold value changes in time as the measured value changes in time;
   establishing a condition value from a combination of said measured value and said dynamic threshold value, wherein said condition value comprises an integrated product of the extent by which said dynamic threshold value is exceeded by said measured value over a quantity of time said dynamic threshold value is exceeded by said measured value;
   triggering an alarm when said condition value exceeds a predetermined level;
   monitoring said alarm when a measured value for said physiological parameter is outside a fixed range;
   establishing a fixed upper threshold value and a fixed lower threshold value, wherein said fixed threshold values define said fixed range;
   determining a quantity of time said measured value is outside said fixed range;
   determining a measure of the amount by which said fixed range is exceeded by said measured value during said quantity of time; and
   triggering said alarm when a combination of said quantity of time and said amount exceeds a second predetermined level.

2. The method of claim 1 wherein said dynamic threshold value tracks said measured value.

3. The method of claim 1 wherein said dynamic threshold value changes continuously in time with changes in time of said measured value.

4. The method of claim 1 wherein said dynamic threshold value changes in time at a rate less than the rate at which said measured value changes in time.

5. The method of claim 1 wherein said dynamic threshold value comprises a lower alarm limit for said measured value.

6. The method of claim 1 wherein said dynamic threshold value comprises an upper alarm limit for said measured value.

7. The method of claim 1 wherein said dynamic threshold value comprises a lower limit and an upper limit for said measured value, and where said lower limit and said upper limit define a range.

8. The method of claim 1 wherein said dynamic threshold value comprises a lower threshold value for said measured value and said establishing said dynamic threshold value further comprises:
   continuously calculating a baseline value of said measured value; and
   computing said lower threshold value by offsetting a value below said baseline value.

9. The method of claim 8 wherein said baseline value is continuously calculated using a filter selected from the group consisting of a low-pass filter, a running median filter, an infinite impulse filter and a finite impulse filter.

10. The method of claim 1 wherein said measured value is an oxygen saturation, and said dynamic threshold value is one of a high oxygen-saturation threshold value and low oxygen-saturation threshold value.

11. The method of claim 1 wherein said measured value is a pulse rate, and said dynamic threshold value is one of a high pulse rate threshold value and a low pulse rate threshold value.

12. The method of claim 1 wherein said dynamic threshold value comprises an upper threshold value for said measured value and said establishing said dynamic threshold value further comprises:
   continuously calculating a baseline value of said measured value; and
   computing said upper threshold value by offsetting a value above said baseline value.

13. The method of claim 12 wherein said baseline value is continuously calculated using a filter selected from the group consisting of a low-pass filter, a running median filter, an infinite impulse filter and a finite impulse filter.

14. A method for controlling an alarm in a pulse oximeter apparatus, said apparatus monitoring said alarm when a measured value for a physiological parameter is outside a specified range, comprising:
   automatically establishing a dynamic upper threshold value and a dynamic lower threshold value, wherein said threshold values define said range, and wherein said dynamic upper and said dynamic lower threshold values are related to a continuously calculated baseline value;
   determining a quantity of time said measured value is outside said range;
   determining a measure of the extent by which said range is exceeded by said value during said quantity of time;
   triggering said alarm when an integrated product of said extent over said quantity of time exceeds a predetermined level;
   further monitoring said alarm when a measured value for said physiological parameter is outside a fixed range;
   establishing a fixed upper threshold value and fixed lower threshold value, wherein said fixed threshold values define said fixed range; and
   triggering said alarm when said measured value exceeds said fixed range by a second predetermined value.

15. A pulse oximeter, comprising:
   an alarm;
   a sensor for measuring a value of a physiological parameter;
   a computer usable medium having computer readable code embodied therein for managing said alarm, said computer readable code configured to execute functions, comprising:

calculating a baseline of said value;

automatically establishing a dynamic upper threshold value and a dynamic lower threshold value, wherein said threshold values define a range, and wherein said dynamic upper and said dynamic lower threshold values are related to said baseline of said value;

determining a quantity of time said measured value is outside said range;

determining a measure of the extent by which said range is exceeded by said measured value during said quantity of time;

triggering said alarm when an integrated product of said extent over said quantity of time exceeds a predetermined level;

further monitoring said alarm when a measured value for said physiological parameter is outside a fixed range;

establishing a fixed upper threshold value and fixed lower threshold value, wherein said fixed threshold values define said fixed range; and triggering said alarm when said measured value exceeds said fixed range by a second predetermined value.

16. The apparatus of claim 15 wherein said measured value is an oxygen saturation, and said range comprises a high oxygen-saturation threshold value and low oxygen-saturation threshold value.

17. The apparatus of claim 15 wherein said measured value is a pulse rate, and said range comprises a high pulse rate threshold value and a low pulse rate threshold value.

* * * * *